(12) United States Patent
Tsuboi et al.

(10) Patent No.: US 6,423,530 B1
(45) Date of Patent: Jul. 23, 2002

(54) PROCESS FOR PREPARING FR900482 AND COMPOUNDS ANALOGOUS THERETO

(75) Inventors: Masaru Tsuboi, Inazawa; Shiho Shimizu, Seto; Michio Yamashita, Tsukuba; Yasuhisa Tsurumi, Tsukuba; Seiji Hashimoto, Tsukuba, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/705,898

(22) Filed: Nov. 6, 2000

Related U.S. Application Data

(62) Division of application No. 09/284,481, filed as application No. PCT/JP97/03907 on Oct. 28, 1997, now Pat. No. 6,204,031.

(30) Foreign Application Priority Data

Oct. 29, 1996 (JP) .............................................. 8-286805

(51) Int. Cl.[7] .............................. C12N 1/14; C12P 17/18
(52) U.S. Cl. ..................... 435/256.5; 435/119; 435/929
(58) Field of Search .............................. 435/119, 256.5, 435/929

(56) References Cited

U.S. PATENT DOCUMENTS 6,204,031 B1 * 3/2001 Tsuboi et al. ................ 435/119

FOREIGN PATENT DOCUMENTS

| EP | 0 144 238 A2 | 6/1985 |
|---|---|---|
| EP | 0 166 389 | 1/1986 |
| JP | 1-101893 | 4/1989 |

OTHER PUBLICATIONS

Itsuo Uschida, et al., "Structure of FR 900482, a Novel Antitumor Antibiotic from a Streptomyces", J. Am. Chem. Soc., vol. 109, No. 13, pp. 4108–4109, 1987.

Shogo Ozawa, et al., "Precursors in the Biosynthesis of FR–900482, A Novel Antitumor Antibiotic Produced by *Streptomyces sandaensis*", The Journal of Antibiotics, vol. 41, No. 3, pp. 392–394, 1988.

Shojiro Iwahara, et al., "Enzymic Oxidation of α, β–Unsaturated Alcohols in the Side Chains of Lignin–related Aromatic Compounds", J. Ferment. Technol., vol. 58, No. 3, pp. 183–188, 1980. XP–002151186.

\* cited by examiner

*Primary Examiner*—Herbert J. Lilling
(74) *Attorney, Agent, or Firm*—Oblon, Spivak, McClelland, Maier & Neustadt, P.C.

(57) ABSTRACT

A process for producing a compound of the general formula (I):

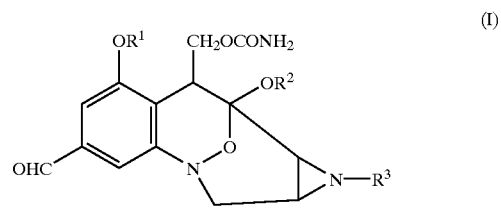

(wherein $R^1$ represents hydrogen, a lower alkanoyl group or a lower alkyl group; $R^2$ and $R^3$ each represents hydrogen or a lower alkanoyl group) characterized in that a compound of the general formula (II):

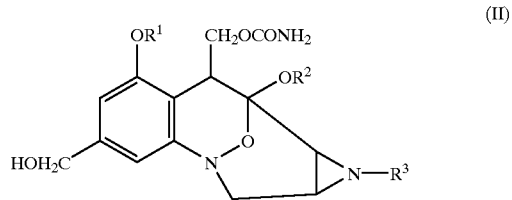

(wherein $R^1$, $R^2$ and $R^3$ are respectively as defined above) is reacted with a culture of a strain of microorganism belonging to the genus Fusarium or its cells harvested by filtering the broth.

3 Claims, No Drawings

PROCESS FOR PREPARING FR900482 AND COMPOUNDS ANALOGOUS THERETO

This application is a Continuation Division Continuation-in-part (CIP) of application Ser. No. 09/284,481 filed on Apr. 22, 1999, pending, which was originally filed as International Application No. PCT/JP97/03907, filed on Oct. 28, 1997, now U.S. Pat. No. 6,204,031.

TECHNICAL FIELD

This invention relates to enzyme technology.

More particularly, the invention relates to a process for oxidizing the alcohol side chain of the following compound (II), which is either a compound elaborated by the microorganism *Streptomyces sandaensis* No. 6897 (FERM BP-792) as such or a chemical transformation product thereof, to thereby transform the compound (II) to the following compound (I) having an aldehyde side chain.

Compound (I) is not only a compound having high antitumoral activity of its own but also a synthetic intermediate of other compounds having antitumoral activity, and there has been a standing demand for a microorganism capable of transforming compound (II) to compound (I) with good efficiency.

DISCLOSURE OF INVENTION

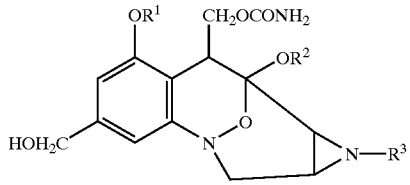

(II)

(wherein $R^1$ represents hydrogen, a lower alkanoyl group or a lower alkyl group; $R^2$ and $R^3$ each represents hydrogen or a lower alkanoyl group)

The inventors of this invention explored extensively for a microorganism which would be able to convert the alcohol side chain of compound (II) to an aldehyde side chain. As a result, they discovered novel oxidase-producing microorganisms in the genus Fusarium and succeeded in converting this substrate to the following compound (I) having an aldehyde side chain.

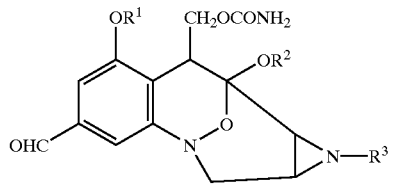

(I)

(wherein $R^1$, $R^2$ and $R^3$ are respectively as defined above).

Among species of compound (I) and compound (II) those compounds having hydrogen for each of $R^1$, $R^2$ and $R^3$ have been named FR900482 and FR066979, respectively. Those compounds are elaborated by the microorganism *Streptomyces sandaensis* No. 6897 (FERM BP-792) and are known compounds having antitumoral and other activities as disclosed in Kokai Tokkyo Koho S61-10590 in Examples 1 and 8 of its specification. Moreover, FR066979 can be produced by the process described in Kokai Tokkyo Koho H1-101893 as well.

FR900482 and FR066979 are the most preferred object compound and starting compound, respectively, of this invention.

Meanwhile, among species of compound (I), the compound having acetyl for each of $R^1$, $R^2$ and $R^3$ has been named FR066973, the compound having hydrogen for each of $R^1$ and $R^2$ and acetyl for $R^3$ has been named FR66980, and the compound having methyl for $R^1$ and acetyl for each of $R^2$ and $R^3$ has been named FR073317, and those compounds are described in Kokai Tokkyo Koho S61-10590 in Examples 3, 4 (and 6), and 51, respectively, of its specification.

While compounds (I) and (II) contain asymmetric carbon within their chemical structures, the isomers due to the asymmetric carbon also fall within the scope of compounds (I) and (II) of the invention.

Referring to the above formulae (I) and (II), the following are the more specific definitions and preferred examples.

Unless otherwise indicated, the term "lower" is used in this specification to mean 1~6 carbon atoms.

The preferred "lower alkanoyl group" includes $C_{1-6}$ alkanoyl groups such as formyl, acetyl, propionyl, butyryl, isobutyryl, valeryl, isovaleryl, pivaloyl, hexanoyl, etc., more preferably $C_{1-4}$ alkanoyl groups, and particularly acetyl.

The preferred "lower alkyl group" includes $C_{1-6}$ alkyl groups such as methyl, ethyl, propyl, isopropyl, butyl, isobutyl, tert-butyl, pentyl, hexyl, etc., preferably $C_{1-4}$ alkyl, and more preferably methyl.

The outstanding features of this invention are now described.

The microorganism according to this invention is first described.

Fusarium sp. No. 122 (Strain F-122)

Characters of Strain F-122

The strain named Fusarium sp. No. 122 (hereinafter abbreviated as Strain No. 122), which is capable of transforming compound (II) to compound (I), was newly isolated from the soil sample collected in Yakushima, Kagoshima-ken. The characters of Strain No. 122 are now described.

This fungus Strain No. 122 was isolated from the soil sample collected in Yakushima, Kagoshima-ken. This microorganism gave broadly diffuse growth on various media and formed white to yellowish white colonies. On various media, Strain No. 122 did not form teleomorphs but formed anamorphs characterized by hyphae bearing phialides (conidiogenous cells) and two types of conidia differing in size, i.e. navicular macroconidia and oval microconidia. The mode of conidiogenesis was phialidic. The mycological characteristics of Strain No. 122 are as follows.

The cultural characteristics on various agar media are summarized in Table 1. On potato dextrose agar, the strain gave broadly diffuse growth, which attained a diameter of 8.0 cm or more by 2 weeks at 25° C. The colony surface was elevated, lanose, and white to yellowish white in color. As to conidia, whereas the microconidia were numerous, the macroconidia were few. The reverse color was yellowish white. On corn meal agar, the strain grew as rapidly as on potato dextrose agar, spreading to a diameter of ≧8.0 cm under the same conditions. The colony surface was protuberant, felty or lanose, and white in color. The conidia, particularly microconidia, were abundantly produced. The reverse color of the colony was white to yellowish white.

The morphological characterization was made on the culture using a sporogenetic medium favoring the formation of macroconidia (medium composition: glycerin 1 g; sodium nitrate 0.5 g; potassium dihydrogen phosphate 0.2 g; yeast extract 0.1 g; agar 15 g; distilled water 1 L). The conidiophores of Strain No. 122 cannot be clearly differentiated from the substrate mycelium, and phialides are directly produced in the form of short branches of the aerial and substrate mycelia. There also are cases in which the substrate hyphae form a dense mass like a sporodochium and phialides occur within or on top of the mass. The phialide is colorless, glabrous, cylindrical to lecythiform, measuring 8~17 (~20)×2~3 µm, and produces macro- and microconidia from its tip in succession. The macroconidia are colorless, glabrous, 2~4 (~6)-celled, navicular or lunate~allantoid, slightly sinuate and acute at both ends, and measuring 25~35 (~42)×3.5~4.5 (~5.5) µm. The microconidium is colorless, glabrous, 1 (~2)-celled, slightly sinuate oval (perprolate), and measuring 6~16 (~20)×2.5~4 µm. The substrate mycelium is glabrous, septate, colorless, and branching. The hypha is cylindrical and 2~3.5 µm in width. Chlamydospores are not formed. When this strain was cultured on Sabouraud's dextrose agar, a black, globose sclerotium is sometimes formed.

Strain No. 122 is able to grow at 2~31° C., with the optimum temperature for growth being 21~25° C. Those data were generated using potato dextrose agar (Nissui).

The above characteristics of Strain No. 122 were compared with the relevant descriptions in the literature on the classification and nomenclature of fungi such as G. R. Barron: The Genera of Hyphomycetes from Soil, pp. 239–241, Williams & Wilkins, Baltimore, 1968; J. A. von Arx: The Genera of Fungi, Sporulating in Pure Culture, pp. 180–184, J. Cramer, Vaduz, 1974; and K. H. Domsch, W. Gams & T. -H. Anderson: Compendium of Soil Fungi, pp. 517–524, Academic Press, London, 1980. The comparison showed agreements with the described characteristics of Fusarium link (1809), suggesting that Strain No. 122 is a strain of microorganism belonging to the genus Fusarium. Accordingly the strain was named Fusarium sp. No. 122. This strain was deposited with National Institute of Bioscience and Human Technology and assigned with the accession number of FERM P-15763 (date of deposit: Aug. 2, 1996), which was subsequently converted to a deposit under Budapest Treaty and assigned with the accession number of FERM BP-6156 (date of deposit: Oct. 23, 1997).

TABLE 1

Cultural characteristics of Strain No. 122

| Medium | Cultural characteristics |
| --- | --- |
| Malt extract agar* | Growth: Widely diffuse, ≧8.0 cm in dia. Surface: Round, flat, felty to floccose, abundant conidia, yellowish white (4A2) Reverse: Yellowish white (3A2) to pale yellow (3A3) |
| Potato dextrose agar (Difco 0013) | Growth: Widely diffuse, ≧8.0 cm in dia. Surface: Round, protuberant, lanose, abundant conidia. White (1A1) to yellowish white (4A2) Reverse: Yellowish white (4A2) |
| Czapek's solution agar* | Growth: Widely diffuse, ≧8.0 cm in dia. Surface: Round, convex to elevated, floccose to lanose, abundant conidia, white (1A1) to yellowish white (4A2) Reverse: Pale yellow (4A3) to light yellow (4A4) |
| Sabouraud's dextrose agar (Difco 0190) | Growth: Widely diffuse, ≧8.0 cm in dia. Surface: Round, flat or elevated, felty to floccose, wrinkled. Abundant conidia, orangy white (6A2) to pale orange (6A3) Reverse: Grayish orange (5B5-5B6) |
| Emerson Yp Ss agar | Growth: Widely diffuse, ≧8.0 cm in dia. Surface: Round, convex to elevated, |

TABLE 1-continued

Cultural characteristics of Strain No. 122

| Medium | Cultural characteristics |
| --- | --- |
| (Difco 0739) | floccose to lanose, pink exudate produced, abundant conidia, white (1A1) to yellowish white (4A2-3A2) Reverse: Yellowish white (3A2) |
| Corn meal agar (Difco 0386) | Growth: Widely diffuse, ≧8.0 cm in dia. Surface: Round, protuberant, felty to lanose, abundant conidia, white (1A1) Reverse: White (1A1) to yellowish white (3A2) |
| MY20 agar* | Growth: Widely diffuse, ≧8.0 cm in dia. Surface: Round, protuberant, felty, abundant conidia, yellowish white (4A2) to orangy white (5A2) Reverse: Grayish orange (4B5-4B6). |

*The compositions of malt extract agar, Czapek's solution agar and MY20 agar were in conformity with JCM Catalog (Nakase, T., 5th ed., 503p., Japan Collection of Microorganisms and Life Science Research Information Section of the Institute of Physical and Chemical Research, Saitama, 1992).

Those data are based on the observation made 14 days of culture at 25° C. The names of colors are based on Methuen Handbook of Colour (Kornerup, A. and J. H. Wanscher, 3rd ed., 525pp., Methuen, London, 1978).

Fusarium sp. No. 104 (Strain F-104)

Characters of Producer Strain F-104

Strain F-104 is a fungal strain owned by the applicant. This microorganism gave widely diffuse growth on various media, forming floccose to lanose, white to reddish white colonies. This strain formed anamorphs on several media but did not form teleomorphs. The anamorph is phialidic, with the slightly branched conidiophore producing two types of conidia (2~5-celled falcate macroconidia and 1~2-celled pyriform microconidia). Looking up those morphological characters in J. A. von Arx's book on the classification of fungi (J. A. von Arx: The Genera of Fungi, Sporulating in Pure Culture, 3rd ed., pp. 145~163, J. Cramer, Vaduz, 1974), the inventors found that Strain F-104 apparently belongs to the genus Fusarium (Fusarium Link 1809) among imperfect fungi. The mycological characteristics of Strain F-104 are as follows.

The cultural characteristics on various agar media are summarized in Table 2. The growth on potato dextrose agar was widely diffuse, attaining a diameter of 6.0~6.5 cm by 2 weeks at 25° C. and forming round colonies. The colony surface was elevated and floccose to lanose. The colony color was white to reddish white with a grayish red margin. The reverse color was brownish purple to purplish brown and, peripherally, pinkish gray to dull red. On this medium, the strain did not form a conidioma. Colony spreads more rapidly on corn meal agar medium under the same conditions as above and spread to more than 9.0 cm in diameter, thus reaching the wall of the dish. The colony expanded radially and circularly and its surface was flat, thin, pulverulent, and pinkish white to pink in color, with a white to pinkish white margin. The substrate mycelium was endogenous (submerged in the substratum) and conidiomata and chlamydospores were sparingly observed. The reverse color was identical with the surface color.

Morphological characterization was made on the basis of the observation on LCA medium in accordance with Miura. K. and M. Kudo: Trans, Mycol. Soc. Japan, 11: 116–118, 1970. The macroconidia and microconidia were produced from the phialides borne by the conidiophore. The conidiophore was colorless, glabrous, septate, more or less monopodial, giving off a few branches and forming conidiogenous cells (phialides) as short branches. The phialide was colorless, glabrous, cylndrical with a slightly narrowed tip, and measured 10~20×3~5 µm. The conidia were produced enteroblastically from the tip of the phialide in basipetal succession, forming slimy masses. The macroconidia are colorless, glabrous, 2~4 (~5)-celled, prominently curved either at both ends or at the tip, falcate to navicular, sometimes with a vesicle at the base, and measured (15~) 23~34 (~43)×3~4.5 (~5) µm. Moreover, frequently cylindrical or slightly curved navicular conidia sized (5~) 10~15× 2.5~3.5 µm were intermingly present. They were colorless, glabrous, 1-celled, and rarely septate 2-celled. The microconidia were colorless, glabrous, 1 (~2)-celled, and pyriform to ellipsoidal, with a rounded but at times slightly pointed tip, and measured 9~13.5 (~18)×4.5~5 (~7) µm. The substrate mycelium was glabrous, septate, colorless, and branched. The hyphae was cylindrical and 2~6 µm wide. On corn meal agar, subglobose to ellipsoidal chlamydosphores were observed among the hyphae and they measured 5~10 µm in diameter.

Strain F-104 was capable of growing at 2~32° C., with the optimum temperature for growth being 21~24° C. The growth data were generated on potato dextrose agar (Nissui Pharmaceutical).

The above mycological characters of the strain were compared with the relevant descriptions in the literature, namely C. Booth: The Genus Fusarium, pp. 237, Commonwealth Mycological Institute, Kew, 1971 and K. H. Domsch, W. Gams & T. -H. Anderson: Compendium of Soil Fungi, pp. 303–341, Academic Press, London, 1980. The results of comparison chiefly with regard to colony color, growth rate, features of the phialide, and morphological characteristics of the macroconidia and microconidia suggested that Strain F-104 belongs to *Fusarium tricinctum* (Corda) Sacc. 1886). Therefore, this strain was identified to be a strain of *Fusarium tricinctum* No. 104. This strain has been deposited with National Institute of Bioscience and Human Technology under the accession number of FERM BP-6155 (date of deposit: Oct. 23, 1997).

TABLE 2

Cultural characteristics of Strain No. 104

| Medium | Cultural characteristics |
|---|---|
| Malt extract agar* | Growth: Slightly isoantagonistic, round, 3.0~3.5 cm in dia. Surface: Flat, hyphae submerged, moist and glabrous. No anamorph formed. Grayish yellow (4B4-4B5) to grayish orange (5B4-5B5) with a brownish orange (5C6) margin. Reverse: Grayish orange (5B4) to brownish orange (5C4) |
| Potato dextrose agar (Difco 0013) | Growth: Widely diffuse, round, 6.0~6.5 cm in dia. Surface: Elevated, floccose to lanose. No anamorph formed. White to reddish white (9A2) with a grayish red margin (8C5-9C5) Reverse: Brownish purple (11D7-11D8) to purplish brown (10E6-10F6) with a pinkish gray (10B2) to dull red (10C3) margin |
| Czapek's solution agar* | Growth: Widely diffuse, round, 7.0~8.0 cm in dia. Surface: Elevated, floccose to lanose. No anamorph formed. White to yellowish white (4A2) with a grayish rose (11B4-11B5) to pinkish white (10A2-11A2) margin. Reverse: Pale yellow (4A3) to grayish yellow |

TABLE 2-continued

Cultural characteristics of Strain No. 104

| Medium | Cultural characteristics |
|---|---|
| | (4B3) centrally and grayish rose (12B6) to grayish rouge (12C6) peripherally. |
| Sabouraud's dextrose agar (Difco 0190) | Growth: Widely diffuse, round, 5.0~6.0 cm in dia. Surface: Elevated to capitate and floccose. No anamorph. White. Reverse: Radially sulcate, grayish orange (5B4) with a light brown (6D6) margin. |
| Emerson Yp Ss agar (Difco 0739) | Growth: Widely diffuse, round, 7.0~8.0 cm in dia. Surface: Elevated, floccose to lanose. Anamorphs are formed. White to yellowish white (4A2) with a pinkish white (10A2) margin. Reverse: Yellowish white (3A2-4A2) with a pastel red (10A4) to dull red (10B4) margin. |
| Corn meal agar (Difco 0386) | Growth: Widely diffuse, round, ≧9.0 cm in dia. Surface: Flat and thin. Hyphae are submerged. Anamorphs and chlamydosphores are sparsely formed. Pinkish white (11A2) to pink (11A5) with a white to pinkish white (9A2) margin. Reverse: the same color as the surface. |
| MY20 agar* | Growth: Widely diffuse, round, 6.0~7.0 cm in dia. Surface: Flat, felty, radially sulcate. No anamorph formed. White with a pale yellow (4A3) margin. Reverse: Reddish yellow (4A6) to grayish yellow (4B6) with a brownish yellow (5C7) to light brown (5D6) margin. |
| Oatmeal agar (Difco 0552) | Growth: Widely diffuse, round, 8.0~9.0 cm in dia. Surface: Elevated, floccose to lanose. Colorless exudate produced. No anamorph formed. Grayish orange (6B3) to orangy gray (5B2) and yellowish white (3A2-4A2). |

*The compositions of malt extract agar, Czapek's solution agar and MY20 agar were in conformity with JCM Catalog (Nakase, T., 5th ed., 503p., Japan Collection of Microogranisms and Life Science Research Information Section of the Institute of Physical and Chemical Research, Saitama, 1992).

The above data are based on the observation made 14 days of culture at 25° C. The names of colors are based on Methuen Handbook of Colour (Rornerup, A. and J. H. Wanscher, 3rd ed., 525p., Methuen, London, 1978).

The process for producing compound (I) is not restricted to the method utilizing the microorganisms herein disclosed for illustrative purposes. Thus, this invention encompasses the use of spontaneous mutants and artificial mutants which can be derived from the above-mentioned microorganisms by the conventional methods for mutagenesis, such as X-ray irradiation, UV irradiation, and treatment with N-methyl-N'-nitro-N-nitrosoguanidine, 2-aminopurine or the like chemical, only provided that such mutants retain the ability to transform compound (II) to compound (I).

The following is a partial list of FR900482-producers other than Fusarium sp. No. 122 and No. 104. The Fusarium strains owned by the applicant:

*Fusarium camptoceras* (F-0500)
*Fusarium equiseti* (F-0499)
*Fusarium graminearum* (F-0497)
*Fusarium oxysporum* f. sp. *lycopersici* (F-0091)
*Fusarium oxysporum* f. sp. *lini* (F-0092)
*Fusarium oxysporum* f. sp. *lini* (F-0094)
*Fusarium oxysporum* (F-0097)

*Fusarium oxysporum* f. sp. *narcissi* (F-0105)
*Fusarium poae* (F-0502)
*Fusarium sambucinum* (F-0498)
*Fusarium solani* var. *coeruleum* (F-0496)
Fusarium sp. F3-1 (F-0183)
*Fusarium sporotrichioides* (F-0503)
The Fusarium strains owned by Institute for Fermentation:
*Fusarium oxysporum* IFO-5942
*Fusarium anguioides* IFO 4467
*Gibberella zeae* (*F. graminearum*) IFO 9462
*Fusarium pallidoroseum* IFO 30926
*Fusarium roseum* IFO 30966
*Fusarium equiseti* IFO 31095
*Fusarium chlamydosporum* IFO 31096
This invention is now described in detail.

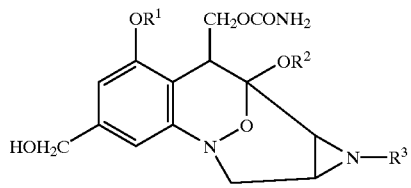
(II)

(wherein $R^1$, $R^2$ and $R^3$ are respectively as defined hereinbefore)

The oxidase produced by the microorganism of this invention oxidizes the alcohol side chain of the compound of formula (II) to give the compound of the following chemical formula (I) (known from Kokai Tokkyo Koho S61-10590). It should be understood that the oxidase need not necessarily be an isolated pure product. Thus, the object compound (I) can be obtained with equal success by culturing the producer microorganism in the presence of compound (II) or using a fermentation broth of the microorganism of the invention, the cells harvested by filtering the broth, or a filtrate or the like available upon separation of the cells from said fermentation broth.

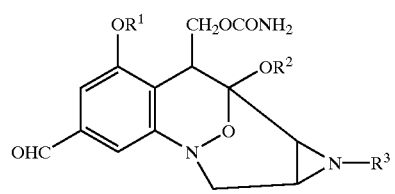
(I)

(wherein $R^1$, $R^2$ and $R^3$ are respectively as defined above).

The fermentation broth, the cells harvested by filtering the broth, or the filtrate available upon separation of the cells from the broth, which is used as the oxidase of the invention, can be obtained by culturing a Fusarium strain, e.g. Fusarium No. 122 or No. 104, in a culture medium.

Generally, those novel microorganisms can be grown in an aqueous medium containing assimilable carbon and nitrogen sources, preferably under aerobic conditions by shake culture or submerged aerobic culture.

The preferred carbon source for use in the medium includes but is not limited to carbohydrates such as glucose, maltose, sucrose, fructose, galactose, mannitol, glycerol, and starch.

The preferred nitrogen source includes organic nitrogenous substances such as soybean meal, cottonseed flour, wheat germ, gluten meal, corn steep powder, peanut flour, linseed oil powder, etc. and inorganic nitrogen compounds such as ammonium nitrate, ammonium sulfate, etc.

While those carbon sources and nitrogen sources are used in a suitable combination, it is not necessary to use purified products but crude substances of low purity can also be used insofar as they contain the corresponding amounts of inorganic nutrients.

If desired, inorganic salts such as potassium phosphate, magnesium sulfate, sodium chloride, iron sulfate, cobalt sulfate, etc. can be added. Particularly when the culture medium produces a copious foam, an antiforming agent such as liquid paraffin, fatty acids, vegetable oil, mineral oil or silicone oil can be added when necessary.

For mass culture of the microorganism, submerged aerobic culture i s preferred. For culture on a small scale, shake bottle culture or surface culture can be used. In the case of tank culture using a large fermentation tank, the tank is preferably inoculated with a seed culture for accelerated growth of the microorganism. Thus, the preferred procedure comprises inoculating a relatively small amount of medium with the conidia or hyphae of the microorganism, incubating the inoculated medium to prepare a seed culture, and transferring the seed culture aseptically to a large tank. The culture medium for use in the preparation of said seed culture may be substantially identical to the medium for tank culture or be a different medium.

The agitation and aeration of the fermentation system can be effected in various ways. The agitation can be effected by using a propeller or equivalent mixing device, rotating or shaking the fermentor, using a suitable pump, or blowing sterile air through the medium. The aeration may be effected by blowing sterile air through the fermentation system.

The fermentation is generally carried out within the temperature range of about 20~32° C., preferably 25~30° C., at pH preferably within the range of 6~8 for about 72~200 hours, although those conditions may be modified as necessary according to the other conditions and scale of fermentation.

The substrate FR066979 in the form of an aqueous solution can be added at the beginning of cultivation or at any other suitable time, and it may be a broth filtrate of low purity.

The transformation product FR900482 can be recovered from the medium by techniques of routine use for the recovery of other known bioactive metabolites. The transformation product FR900482 exists in the culture filtrate and can be separated and purified by filtration or centrifugation of the fermentation broth and subsequent routine procedures such as a conventional resin treatment using, for example, an adsorbent resin, crystallization and so forth.

EXAMPLES

Example 1

A 500-mL conical flask containing 100 mL of a seed culture medium of the composition: cottonseed flour 1%, soybean meal 1%, ammonium nitrate 0.1%, potassium dihydrogen phosphate 0.1%, magnesium sulfate, heptahydrate 0.05%, sodium chloride 0.1%, and ferric sulfate heptahydrate 0.001% was sterilized at 121° C. for 20 minutes, then inoculated with 1~2 loopfuls of a slant agar culture of Fusarium sp. No. 122 and incubated under shaking at 25° C. for 2 days to prepare a seed culture.

Then, a production medium of the composition: maltose monohydrate 5%, soybean meal 2%, potassium dihydrogen phosphate 0.1% and magnesium sulfate heptahydrate 0.05% was adjusted to pH 6.0 and a 100-mL conical flask was charged with 10 mL of the above production medium and sterilized at 121° C. for 20 minutes. This flask was inoculated with 0.5 mL of the above seed culture and incubated under shaking at 30° C. for 3 days. Then, 0.3 mL of 10 mg FR066979/mL aqeous solution was added and the flask was further incubated under shaking for 3 days to effect transformation of the substrate to FR900482.

Then, this fermentation broth was filtered through No. 2 filter paper and using a high-performance liquid chromatograph (HPLC) equipped with a UV detector (wavelength 215 nm), FR900482 was monitored to determine its yield.

Example 2

A 500-mL conical flask containing 100 mL of a seed culture medium of the composition: cottonseed flour 1%, soybean meal 1%, ammonium nitrate 0.1%, potassium dihydrogen phosphate 0.1%, magnesium sulfate heptahydrate 0.05%, sodium chloride 0.1%, and ferric sulfate heptahydrate 0.001% was sterilized at 121° C. for 20 minutes, inoculated with 1~2 loopfuls of a slant agar culture of Fusarium sp. No. 122, and incubated under shaking at 25° C. for 2 days to prepare a seed culture.

Then, a production medium of the composition: maltose monohydrate 5%, soybean meal 2%, potassium dihydrogen phosphate 0.1% and magnesium sulfate heptahydrate 0.05% was adjusted to pH 6.0 and a 100-mL conical flask was charged with 10 mL of the above production medium and sterilized at 121° C. for 20 minutes. This flask was inoculated with 0.5 mL of the above seed culture, followed by addition of 0.3 mL of 10 mg FR066979/ml aqueous soulution. The flask was incubated under shaking for 8 days to effect transformation of the substrate to FR900482.

Then, this fermentation broth was filtered through No 2 filter paper and using a high-performance liquid chromatograph (HPLC) equipped with a UV detector (wavelength 215 nm), FR900482 was monitored to determine its yield.

Transformation of FR066979 to FR900482 by Strain No. 12222

1. Cultural Conditions

Seed Culture
  Medium composition Pharmamedia 1%, soybean meal 1%, $NH_4NO_3$ 0.1%, $KH_2PO_4$ 0.1%, $MgSO_4 \cdot 7H_2O$ 0.05%, NaCl 0.1%, $FeSO_4 \cdot 7H_2O$ 0.001%, pH 6.0; city water; sterilized by autoclaving at 121° C. for 20 minutes.
  Cultural conditions A 500-mL conical flask containing 100 mL of the above medium was inoculated with 1 loopful and incubated at 25° C. for 2 days with shaking at 260 rpm and 2-inch stroke.

Production Culture
  Medium composition Maltose·$1H_2O$ 5%, soybean meal 2%, $KH_2PO_4$ 0.1%, $MgSO_4 \cdot 7H_2O$ 0.05%, adjusted to pH 6.0, city water; sterilized by autoclaving at 121° C. for 20 minutes.
  Cultural conditions A 100-mL conical flask containing 10 mL of the above medium was inoculated with 5 volume % of seed culture and incubated at 30° C. for ~8 days with shaking at 260 rpm and 2-inch stroke.

Substrate FR066979, 10 mg/mL solution (sterilized by filtration)
  Using a pipette, the substrate was added at a final concentration of 300 μg/mL at the beginning of culture.

2. HPLC Analysis of FR066979 and FR900482
  Column: Mightysil RP-18 75-4.6 (5 μm), Kanto Kagaku K.K.
  Mobile phase: 7.2 mM $SDS/H_2O$ (700): acetonitrile (300): phosphoric acid (1)
  Detection: UV 215 nm
  Flow rate: 1.0 mL/min.

3. Study Items

1) The kind and concentration of carbon source
  2) The kind of organic nitrogen source
  3) Medium pH
  4) Working Volume
  5) Incubation temperature
  6) The level of addition of FR066979
  7) Time course 4. Results 4-1. The Effect of Carbon Sources and its Concentration This effect was investigated with 10 kinds of carbon sources. When maltose or mannitol was used as the carbon source, the transformation yield was remarkably high (Table 3).

TABLE 3 effect of carbon sources μg/ml

| C source | 6th 482*) | 6th 979**) | 8th 482 | 8th 979 |
| --- | --- | --- | --- | --- |
| Glucose | 45 | 215 | 87 | 166 |
| Sucrose | 47 | 244 | 81 | 196 |
| Soluble starch | 34 | 214 | 45 | 176 |
| Glycerol | 73 | 181 | 91 | 142 |
| Galactose | 41 | 210 | 73 | 159 |
| Maltose | 102 | 146 | 161 | 40 |
| Dextrin | 47 | 222 | 75 | 166 |
| Sorbose | 4 | 110 | 7 | 106 |
| Mannitol | 101 | 157 | 164 | 105 |
| Fructose | 26 | 183 | 50 | 160 |

*) 482: FR900482,
**) 979: FR066979

The effect of concentration of maltose was then investigated. As a result, the highest transformation yield was obtained at 5% concentration (Table 4).

TABLE 4

Effect of maltose concentration μg/ml

| Maltose % | 6th 482 | 6th 979 | 8th 482 | 8th 979 |
| --- | --- | --- | --- | --- |
| 0 | 14 | 215 | 16 | 203 |
| 2.5 | 93 | 125 | 88 | 102 |
| 5 | 67 | 186 | 105 | 113 |
| 7.5 | 62 | 198 | 91 | 160 |
| 10 | 27 | 231 | 42 | 208 |

4-2. The Effect of Organic Nitrogen Source

This effect was investigated for 12 kinds of organic nitrogen sources. As a result, comparatively high transformation rates were obtained for soybean meal, dried yeast, defatted wheat germ and defatted soybean flour.

TABLE 5

Effect of organic nitrogen sources μg/ml

|  | 6th | | 8th | |
|---|---|---|---|---|
| N source | 482 | 979 | 482 | 979 |
| Control (no addition) | 17 | 235 | 30 | 214 |
| Soybean meal | 103 | 128 | 136 | 97 |
| Pharmamedia | 79 | 163 | 72 | 146 |
| Corn steep liquor | 0 | 178 | 0 | 154 |
| Corn steep powder | 15 | 188 | 21 | 178 |
| Dried yeast | 79 | 146 | 105 | 95 |
| Potato protein | 30 | 215 | 49 | 131 |
| Defatted wheat germ | 59 | 195 | 161 | 59 |
| Wheat germ | 30 | 233 | 76 | 169 |
| Gluten meal | 20 | 244 | 61 | 171 |
| Defatted soybean flour | 93 | 121 | 112 | 75 |
| Peanut flour | 62 | 198 | 87 | 180 |
| Linseed oil cake | 101 | 115 | 63 | 130 |

4-3. The Effect of the Initial pH of Medium (Table 6)

TABLE 6

Effect of pH μg/ml

|  | 6th | | 8th | |
|---|---|---|---|---|
| pH | 482 | 979 | 482 | 979 |
| 5 | 70 | 202 | 103 | 158 |
| 5.5 | 80 | 186 | 122 | 124 |
| 6 | 59 | 192 | 85 | 158 |
| 6.5 | 60 | 193 | 76 | 167 |
| 7 | 52 | 198 | 77 | 159 |
| 7.5 | 47 | 184 | 75 | 136 |
| 8 | 46 | 168 | 62 | 129 |

4-4. The Effect of Working Volume (Table 7)

TABLE 7

Effect of Working Volume μg/ml

|  | 6th | | 8th | |
|---|---|---|---|---|
| Batch size, mL | 482 | 979 | 482 | 979 |
| 10 | 100 | 151 | 125 | 109 |
| 15 | 58 | 184 | 100 | 135 |
| 20 | 56 | 189 | 75 | 166 |
| 25 | 30 | 206 | 48 | 175 |
| 30 | 39 | 210 | 52 | 183 |

4-5. The Effect of Incubation Temperature (Table 8)

TABLE 8

Effect of incubation temperature μg/ml

|  | 6th | | 8th | |
|---|---|---|---|---|
| Temperature, °C. | 482 | 979 | 482 | 979 |
| 25 | 51 | 143 | Not Tested | |
| 30 | 60 | 143 | | |
| 32 | 109 | 61 | | |
| 35 | 0 | 303 | | |

4-6. The Effect of the FR066979 Concentration (Table 9)

TABLE 9

Effect of the FR066979 concentration μg/ml

|  | 6th | | 8th | |
|---|---|---|---|---|
| FR066979, μg/mL | 482 | 979 | 482 | 979 |
| 100 | 35 | 35 | Not Tested | |
| 200 | 82 | 53 | | |
| 400 | 177 | 97 | | |
| 500 | 216 | 106 | | |
| 600 | 179 | 223 | | |

4-7. Time Course

The time course of transformation from FR066979 to FR900482 was investigated at 25° C. and 30° C. By 8-day culture, about 40–50% of FR066979 was transformed to FR900482 (Table 10).

TABLE 10

Time course μg/ml

|  | 25° C. | | 30° C. | |
|---|---|---|---|---|
| Time (d) | 492 | 979 | 492 | 979 |
| 0 | 0 | 262 | 0 | 262 |
| 1 | 0 | 255 | 0 | 263 |
| 2 | 0 | 260 | 0 | 259 |
| 3 | 19 | 245 | 13 | 244 |
| 4 | 44 | 212 | 48 | 206 |
| 5 | 67 | 183 | 82 | 161 |
| 6 | 68 | 174 | 110 | 112 |
| 7 | 92 | 135 | 124 | 76 |
| 8 | 108 | 114 | 130 | 56 |

Example 3

Ten (10) liters of a fermentation broth of *Streptomyces sandaensis* No. 6897 grown in accordance with Kokai Tokkyo Koho H1-101893 was filtered and the cells were rinsed with water to provide a total of 10 L of filtrate. This filtrate contained FR900482 and FR066979 in a combined concentration of about 1 mg/mL.

The filtrate was passed over 5 L of synthetic adsorbent resin, e.g. SEPABEADS SP850 or SEPABEADS SP207. After the resin was irrigated with water to remove the protein, amino acid, and salt, FR900482 and FR066979 were eluted with 20 L of 50% methanol/H$_2$O.

This methanol/H$_2$O fraction was concentrated to 1.5 L and added to 10 L of a culture of Fusarium sp. No. 122. The reaction for transformation from FR066979 to FR900482 was thus carried out until the concentration of FR066979 had droppedbelow the detection limit (after about 15 hours). The concentration of FR900482 was about 730 μg/mL.

The reaction mixture was filtered and the filtrate, 11 L, was passed over 2 L of the adsorbent resin DIAION HP20. After the protein, amino acid and salts were rinsed with 10% methanol/H$_2$O, elution was carried out with 20 L of 0.05 N-sulfuric acid. The concentration of FR900482 was 370 μg/mL.

This active fraction was concentrated to 10 L and passed over 5 L of the adsorbent resin DIAION HP1MG. After the resin was washed with 40 L of water, FR900482 was eluted with 15 L of 50% methanol/H$_2$O.

The active fraction was concentrated to 8 L and adjusted to pH 7 with 6 N-NaOH. Following the addition of 8 L of ethyl acetate and 12 mL of acetic anhydride under stirring, the reaction was carried out at room temperature for 30 minutes. The reaction was completed when the residual FR900482 ceased to be detected, and the product FR066980 was extracted into ethyl acetate.

After this ethyl acetate layer was concentrated to 75 mL, 75 mL of pyridine and 16 mL of acetic anhydride were added, and the reaction for transformation from FR066980 to FR066973 was carried out at 40° C. with stirring for 15 hours. After 95% or higher conversion rate was obtained, the reaction system was brought to pH 3 with 6 N-hydrochloric acid to complete the reaction. 500 mL of water was added to this reaction mixture whereby the pyridine was removed into the aqueous layer under acidic conditions. To the organic layer, 500 mL of 10% sodium hydrogencarbonate suspension was added, and the unreacted acetic anhydride and acetic, acid were removed into the aqueous layer. Approximately 6 g of the product FR066973 was contained in the ethyl acetate layer.

6 g of activated carbon was added to the 75 mL of ethyl acetate layer for decolorization. Then, the carbon was filtered off and 375 mL of n-hexane was added to the filtrate. This liquid was passed through 5 mL of YMC-GEL silica gel (YMC Co., Ltd.) column to absorb, and elution was carried out with 25 mL of ethyl acetate:n-hexane (5:1).

The eluted fraction was concentrated to dry and was dissolved in 80 mL of acetone. Then, 120 mL of n-hexane was added at room temperature with stirring and the mixture was allowed to stand for about 2 hours, whereby 5 g of FR066973 were obtained as crystals.

Using 5 g of this FR066973, the synthetic procedure described in Kokai Tokkyo Koho S61-10590 was repeated to obtain 1 g of FR073317.

Determination of FR066973 and FR073317 by HPLC

The HPLC equipped with a variable-wavelength UV detector (Shimadzu SPD-10A), a pump (Shimadzu LC-10AD) and an integrator (Shimadzu C-R6A) were used. The stationary phase was TSKgel ODS 80™ (4.6 mm×150 mm i.d., bead dia. 5 μm) and the mobile phase was acetonitrile/0.1 M perchlorate buffer (pH 3.0)=1:3. FR066973 and FR073317 were eluated at a flow rate of 1.4 mL/min. UV detection was made at 220 nm. The retention time of FR066973 was about 5.1 minutes and that of FR073317 was about 4.7 minutes.

Example 4
(1) Strains
All the 8 stains used in the screening were procured from Institute for Fermentation (IFO).

*Fusarium anguioides* IFO 4467

*Gibberella zeae* (F. graminearum) IFO 9462

*Fusarium pallidoroseum* IFO 30926

*Fusarium roseum* IFO 30966

*Fusarium equiseti* IFO 31095

*Fusarium chlamydosporum* IFO 31096

*F. tricinctum* (F-104) (Fusarium sp. No. 104) has been deposited with National Institute of Bioscience and Human Technology.

(2) Medium and cultural conditions

|  | Seed culture |  | Production culture |  |
|---|---|---|---|---|
| Medium composition | Pharmamedia | 1% | Maltose.1H$_2$O | 5% |
|  | Defatted soybean flour | 1% | Defatted soybean flour | 2% |
|  | NH$_4$NO$_3$ | 0.1% | KH$_2$PO$_4$ | 0.1% |
|  | KH$_2$PO$_4$ | 0.1% | MgSO$_4$.7H$_2$O | 0.5% |
|  | MgSO$_4$.7H$_2$O | 0.05% |  |  |
|  | NaCl | 0.1% | pH | 6 |
|  | FeSO$_4$.7H$_2$O | 0.001% |  |  |
| Batch size | 100 ml |  | 10 ml |  |
| Fermentor | Conical flask, 500 mL capacity |  | Conical flask, 100 mL capacity |  |
| Inoculum | 10 mm cube of agar slant |  | 4 vol. % of seed culture |  |
| Incubation temperature | 25° C. |  | 25° C. |  |
| Incubation time, days | 3 |  | 6~8 |  |

(3) Screening Method
(3-1) The production medium containing 300 μg/mL of filtration-sterilized FR066979 added ahead of time was inoculated with the seed culture and incubated under shaking at 25° C. for 8 days. On completion of culture, 50 μL of 15 N-H$_2$SO$_4$ was added and the mixture was centrifuged at 2,800 rpm for 10 minutes. FR900482 in the supernatant was assayed by HPLC.

(3-2) The production medium was inoculated with the seed culture and incubated under shaking at 25° C. for 3 days. Then, filtration-sterilized FR066979 was added at a final concentration of 300 μg/mL and the shake culture was continued at 25° C. for another 3 days. The fermentation broth was treated in the same manner as (1) and FR900482 in the supernatant was assayed by HPLC.

(4) Results
The data in Tables 11 and 12 indicate that microorganisms harboring the enzyme capable of oxidizing the alcohol side chain of FR066979 exist with a remarkably high probability among microorganisms of the genus Fusarium.

TABLE 11

Production of FR900482 from FR066979 added at the beginning of culture

| Strain of microorganism | FR900482 | FR066979 |
|---|---|---|
| *Fusarium anguioides* IFO 4467 | 147 | 6 |
| *Gibberella zeae* IFO 9462 | 121 | 29 |
| *Fusarium pallidoroseum* IFO 30926 | 97 | 69 |
| *Fusarium roseum* IFO 30966 | 152 | 10 |
| *Fusarium equiseti* IFO 31095 | 15 | 224 |
| *Fusarium chlamydosporum* IFO 31096 | 19 | 0 |
| *Fusarium tricinctum* F-104 | 155 | 0 | unit: μg/mL

TABLE 12

Production of FR900482 from FR066979 added in the course of culture (by the method 3-2)

| Strain of microorganism | FR900482 | FR066979 |
|---|---|---|
| *Fusarium anguioides* IFO 4467 | 163 | 15 |
| *Gibberella zeae* IFO 9462 | —* | — |
| *Fusarium pallidoroseum* IFO 30926 | 35 | 221 |
| *Fusarium roseum* IFO 30966 | 196 | 6 |

TABLE 12-continued

Production of FR900482 from FR066979 added in
the course of culture (by the method 3-2)

| Strain of microorganism | FR900482 | FR066979 |
|---|---|---|
| *Fusarium equiseti* IFO 31095 | 0 | 298 |
| *Fusarium chlamydosporum* IFO 31096 | 72 | 12 |
| *Fusarium tricinctum* F-104 | 231 | 31 | unit: μg/mL

—*: No data

As described above, FR900482 can be produced from FR066979 in high yield.

What is claimed is:

1. A biologically pure culture of Fusarium sp. No. 122 or *Fusarium tricinctum* No. 104.

2. The culture of claim 1, which is of Fusarium sp. No. 122.

3. The culture of claim 1, which is of *Fusarium tricinctum* No. 104.

\* \* \* \* \*